(12) United States Patent
Dupuy et al.

(10) Patent No.: US 10,746,678 B2
(45) Date of Patent: Aug. 18, 2020

(54) DEW POINT AND CARRY-OVER MONITORING

(71) Applicant: EQUINOR ENERGY AS, Stavanger (NO)

(72) Inventors: Pablo Matias Dupuy, Hommelvik (NO); Audun Faanes, Trondheim (NO); Oddbjørn Rekaa Nilssen, Trondheim (NO); Torbjørn Vegard Løkken, Trondheim (NO)

(73) Assignee: EQUINOR ENERGY AS, Stavanger (NO)

( * ) Notice: Subject to any disclaimer, the term of this patent is extended or adjusted under 35 U.S.C. 154(b) by 90 days.

(21) Appl. No.: 15/557,298

(22) PCT Filed: Mar. 16, 2016

(86) PCT No.: PCT/NO2016/050049
§ 371 (c)(1),
(2) Date: Sep. 11, 2017

(87) PCT Pub. No.: WO2016/148578
PCT Pub. Date: Sep. 22, 2016

(65) Prior Publication Data
US 2018/0052126 A1 Feb. 22, 2018

(30) Foreign Application Priority Data
Mar. 17, 2015 (WO) ............... PCT/GB2015/050774

(51) Int. Cl.
G01N 25/00 (2006.01)
G01K 1/00 (2006.01)
(Continued)

(52) U.S. Cl.
CPC ............... *G01N 25/68* (2013.01); *G01N 9/36* (2013.01); *G01N 33/225* (2013.01); *G01N 21/85* (2013.01)

(58) Field of Classification Search
USPC ............................. 374/16, 27, 141, 208, 143
See application file for complete search history.

(56) References Cited

U.S. PATENT DOCUMENTS 2,106,593 A 1/1938 Deniston et al.
6,327,890 B1 12/2001 Galipeau et al.
(Continued)

FOREIGN PATENT DOCUMENTS

JP 55-158539 12/1980
WO 2007/046139 4/2007

OTHER PUBLICATIONS

Translation of WO 2007/046139A1 (equivalent translation is JP4672019) (Year: 2007).*
(Continued)

Primary Examiner — Mirellys Jagan
(74) Attorney, Agent, or Firm — Wenderoth, Lind & Ponack, L.L.P.

(57) ABSTRACT

The invention relates to a method for automatically monitoring the liquid content in a gas, and in particular the gas leaving a scrubber and entering a compressor. In the method, a sample of fluid is taken from the outlet of the compressor, its temperature and pressure are automatically varied, and the pressure and temperature at which condensation forms is automatically detected. The pressure and temperature thus detected can be used to determine the liquid content in the gas. In a variant method, the temperature and pressure of the sample are automatically varied, and the rate of liquid condensation is measured to determine the liquid content. The invention also extends to a device for cooling a gas so that the liquid content of the gas can be determined, includ- (Continued)

ing a cooled housing with a cavity therein, and means for measuring the temperature and pressure within the cavity.

6 Claims, 7 Drawing Sheets

(51) Int. Cl.
<br>  *G01N 25/68*  (2006.01)
<br>  *G01N 33/22*  (2006.01)
<br>  *G01N 9/36*  (2006.01)
<br>  *G01N 21/85*  (2006.01)

(56) References Cited

U.S. PATENT DOCUMENTS

| | | | |
|---|---|---|---|
| 7,452,390 B1* | 11/2008 | Al-Khalifa | F17C 7/02 137/13 |
| 7,581,877 B1 | 9/2009 | Zarrabian | |
| 2003/0177785 A1* | 9/2003 | Kimble | F25J 1/0022 62/613 |
| 2010/0037678 A1 | 2/2010 | Chothani et al. | |
| 2015/0233634 A1* | 8/2015 | Zubrin | H04W 76/10 62/619 |
| 2015/0292403 A1* | 10/2015 | Denton | F02C 3/20 60/772 |
| 2015/0300301 A1* | 10/2015 | Lee | B63B 25/16 123/445 |
| 2019/0024003 A1* | 1/2019 | Steill | C07C 9/04 |
| 2020/0017741 A1* | 1/2020 | Novek | F25J 1/0211 |

OTHER PUBLICATIONS

International Search Report dated Jun. 17, 2016 in International Application No. PCT/NO2016/050049.
Written Opinion of the International Searching Authority dated Jun. 17, 2016 in International Application No. PCT/NO2016/050049.
International Search Report issued in International Application No. PCT/GB2015/050774 dated Jul. 9, 2015.
Written Opinion of the International Searching Authority issued in International Application No. PCT/GB2015/050774 dated Jul. 9, 2015.
Wilkes, C. et al., "Gas Fuel Conditioning System Design Considerations for Utility Gas Turbines", Proceedings of the 1997 International Gas Turbine & Aeroengine Congress & Exposition, 1997, ISSN 0402-1215, pp. 4, 6 and 7 and figure 6.

* cited by examiner

DEW POINT AND CARRY-OVER MONITORING

The invention relates to a method for monitoring the liquid content in gas entering a compressor, and more particularly to monitoring the liquid content in gas exiting a scrubber before it enters a compressor.

It is often necessary to measure the liquid content of a process stream. For example, WO 2007/046139 (Kawasaki Plant Systems KK) discloses a system in which fuel gas used as a power source in a land-based power generation plant is monitored to determine the amount of water in the gas stream. In this system, measurement is relatively straightforward, as the amount of liquid in the gas stream is relatively large, and condensed water is stable at normal atmospheric conditions.

In particular, during the extraction of natural gas, it is important to measure the amount of liquid chemicals, oil, condensed hydrocarbons and/or water in the gas, to meet quality specifications. Further, the presence of too much liquid in the gas can cause serious damage to equipment intended to operate on gas (such as compressors). It is particularly important to measure the liquid content of gas emerging from a gas scrubber or other device for separating liquid from the gas, to monitor the performance of the scrubber, and to avoid damage to the compressor. The amount of liquid in the gas is normally quite small (usually in the range of 0.01 to 10 parts per million).

A scrubber which is close to being overloaded can be a bottleneck in a production facility, and may for example limit the maximum amount of gas that can be produced. It is thus very useful to know how much liquid is in the gas exiting the scrubber (often referred to as "carryover") when evaluating the need for modification in the facility.

One way of assessing the amount of liquid in the gas (the carryover) is through a manual dew point sensor (such as a chilled mirror hygrometer). In a sensor of this type, a sample of gas is taken from a process stream, and the pressure of the gas is reduced. The low pressure gas is then passed over a cold surface, usually a mirror. If the pressure and temperature of the sample are at appropriate levels, then condensation will form on the cold surface, and the presence (or absence) of condensation can be detected by observation with the naked eye.

The pressure and temperature at which condensation forms is referred to as the dew point line, and will vary depending on the amount of liquid in the gas. Thus, it is possible to determine the amount of liquid in the gas by varying the pressure and temperature until condensation occurs, and then using the pressure and temperature at which condensation forms to determine the amount of liquid in the gas. Quantification of the amount of liquid can be achieved with the help of an off-line gas composition. The process is carried out at discrete intervals (during a particular hour on a given day), rather than continuously, and so it cannot take account of carryover at a different time.

Online dew point sensors are known, and are normally installed on export gas lines to check that the gas complies with required dew point specifications. These online dew point sensors cannot use naked-eye observations of condensation on a cold mirror; instead, various other methods of detecting the presence of condensation on a cold surface, such as those discussed in U.S. Pat. No. 6,126,311 and US 2011/0188535, can be used. So far, online sensors of this type have not been used for online monitoring of liquid carryover from scrubbers.

Another problem with using assessing carryover via sampling two-phase (liquid in gas) flows in this way is that it is difficult to guarantee that the sample taken from the flow is representative. For example, the sample taken may well have more or less liquid than the average amount.

According to a first aspect of the invention, there is provided a method of monitoring the dew point at the outlet of a compressor, comprising the steps of: taking a sample of fluid from the outlet of the compressor, the fluid being in a supercritical state or a superheated gas; passing the sample through a regulator to thereby change the flow rate and pressure of the sample, and passing the sample through a temperature changing means to thereby change the temperature of the sample; varying the pressure and temperature of the sample and detecting the pressure and temperature at which condensation forms; wherein the variation of the pressure and temperature and the detection is carried out automatically.

With this method, the fluid sample is taken from the outlet of the compressor in a uniform superheated single phase. There is thus no risk of the sample having an anomalously high or low liquid fraction.

In one form of the invention, the sample is passed over a cold surface, the temperature of which can be varied automatically, and the pressure and temperature at which condensation forms on the cold surface is detected automatically.

As the pressure and temperature of the sample are varied automatically, and the detection of the pressure and temperature at which condensation forms is also carried out automatically, the entire monitoring process can be carried out without human intervention. This allows continuous monitoring of the compressor outlet, and so an alarm can be given as soon as anything untoward is detected. It also allows monitoring of flows in areas which are inaccessible or dangerous. Logged carryover can also be correlated to other operational parameters such as chemical levels and scrubber liquid level.

Any suitable method of detecting the condensation can be used; however, it is preferred for the detection to be carried out using a method that can provide additional information regarding the type of liquid phase which has formed, such as optical means, and more preferably near infra-red absorption or Raman spectroscopy. These methods have the advantage that absorption is different for water and hydrocarbon condensate, and so it is possible to determine what liquid has condensed. Further, the wavelengths used can pass through heavy oil, and thus the detection technique is robust with regard to fouling of the cold surface.

In a preferred form, the compressor is directly downstream of a scrubber, and the pressure and temperature at which condensation forms is used to determine the amount of liquid in the gas exiting the scrubber.

This allows a more convenient monitoring of the outlet of the scrubber. As discussed above, sampling a two-phase flow of gas with carryover brings the disadvantage that the sample may not be representative of the entire flow. By allowing the compressor to heat and compress the flow of gas with carryover into a uniform state (superheated gas or supercritical state), it is possible to be more sure that the sample is representative of the flow.

In one form, the temperature of the sample is reduced by passing the sample back to the scrubber, and using the scrubber as the cold source in a heat exchanger with the sample as the hot fluid.

Since the sample is in a supercritical state, or is a superheated gas, it is necessary to cooling the sample to a point where condensation can takes place. It is possible to provide a separate cooler for this purpose; however, it may be preferable to use the relatively cool flow in the scrubber to cool the sample, as this avoids the need for a separate cooler.

According to a second aspect of the present invention, there is provided a method of monitoring the liquid content in a gas stream downstream of a superheating unit, comprising the steps of: taking a sample of fluid downstream of the superheating unit, the fluid being in a supercritical state or a superheated gas; passing the sample through a regulating arrangement to change the flow rate and pressure of the sample, and passing the sample through a heat exchanger to change the temperature of the sample; and measuring the rate of liquid condensation; wherein the variation of the pressure and temperature and the measurement is carried out automatically.

As with the first aspect, the fluid sample is taken from the outlet of the compressor in a uniform superheated single phase, and so there is no risk of the sample having an anomalously high or low liquid fraction. Further, the entire monitoring process can be carried out without human intervention.

Measuring the rate of liquid condensation provides an additional route to determining the liquid content. Any suitable means may be provided for measuring the rate of liquid condensation, but in a preferred form, the measurement is carried out by a densitometer, and preferably an oscillating U-tube densitometer.

The superheating unit may be a compressor or a heater.

The invention also extends to a system for carrying out the methods defined above.

According to a third aspect of the present invention, there is provided a device for cooling a gas so that the liquid content of the gas can be determined, including: a housing disposed in contact with a cold source such as a heat sink; a cavity within the housing, in which cavity the gas is cooled so that the liquid can condense and be separated from the gas; an inlet for the gas at the top of the cavity; an outlet for the gas at the lower part of the cavity; an outlet for condensed liquid at the bottom of the cavity, wherein said outlet for condensed liquid can be connected to a densitometer; and means for measuring the temperature and pressure within the cavity.

This device provides an integrated cooler and separator, which cools the sample so that condensation takes place, and separates the condensed liquid from the gas. The condensed liquid can be analyzed by the densitometer, which provides a further measurement of the amount of liquid in the gas stream. The integrated cooler-separator is compact and simplifies the apparatus.

In a preferred form, the cavity includes a large number of posts, which increase the surface area of the cavity. This improves the heat transfer characteristics of the device, and allows more cooling of the sample.

The posts may be formed integrally with the walls of the cavity. However, in a preferred form, the posts are provided as part of one or more inserts which can be removably fitted into the cavity.

This aspect also extends to the device in combination with a densitometer.

Preferred embodiments of the invention will now be described by way of example only and with reference to the attached Figures, in which.

Figure 1:
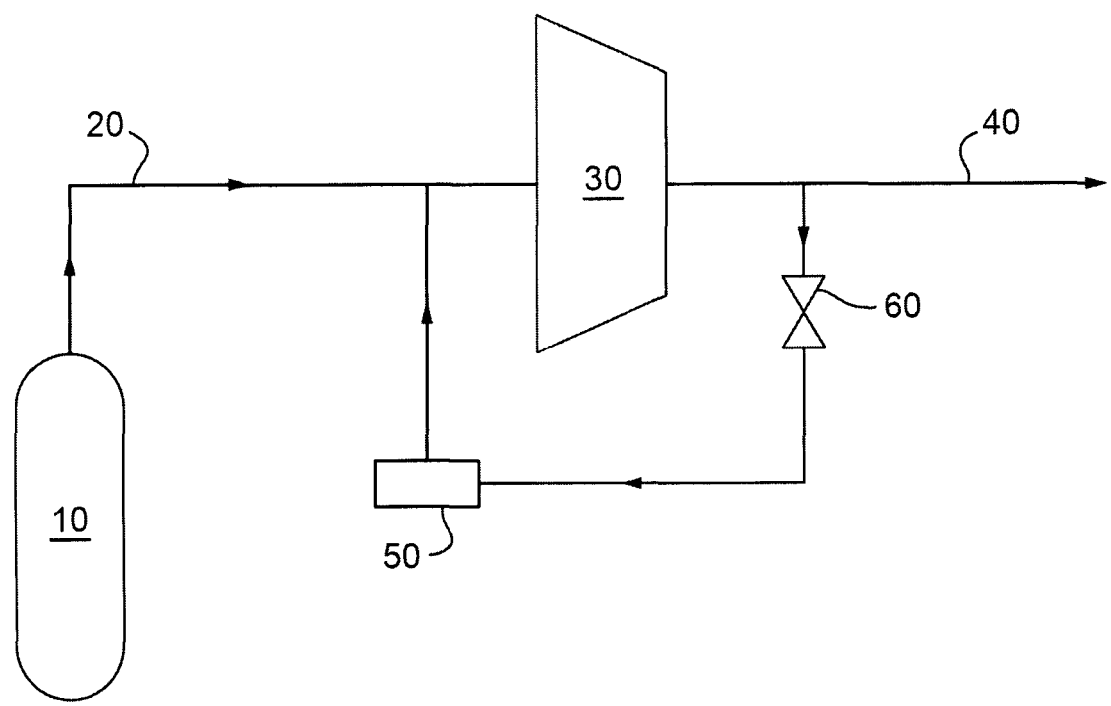
FIG. 1 is a schematic view of the dew point monitoring apparatus of the present invention installed in the vicinity of a scrubber and a compressor for monitoring the carry-over from the scrubber.

As shown in FIG. 1, a scrubber or separator 10 is provided to remove liquid from a gas flow. The dried gas exiting the scrubber then passes along line 20 to a compressor 30. The compressed gas leaves the compressor along line 40. As a result of the compression, the compressed gas leaving the compressor is a single phase (corresponding to a supercritical fluid); any residual liquid (carryover) entering the compressor with the dried gas will also be present as supercritical fluid.

A dew point sensor 50 is provided to monitor the amount of liquid in the gas stream exiting the scrubber 10. A small amount of the compressed gas is bled from line 40 downstream of the compressor 30, passes through a regulating valve 60, and then passes through the dew point sensor 50. The gas leaving the dew point sensor 50 is readmitted to line 20 or to scrubber 10 (optionally via a valve), upstream of the compressor. It is also possible to flare or dump the gas leaving the sensor, but this is wasteful and is not preferred.

Compressors routinely include small nozzles or connectors in the piping upstream and downstream of the compressor, and so there is no difficulty in installing the system in existing plants. It is also possible to install the sensor in association with a surge control loop, which in practice will be present on the compressor.

The dew point sensor 50 operates in a similar manner to a manual dew point sensor, in that the gas is passed over a cold surface, and condensation on the surface is detected. However, rather than relying on naked-eye observations to determine the presence of condensation, a different form of sensing means is used.

The regulating valve 60 (and the valve between the sensor 50 and the line 20 or the scrubber 10, if such a valve is present) can be used to vary the pressure of the gas at the outlet of regulating valve 60. The pressure at the outlet of regulating valve 60 can be varied between the compressor suction pressure (the pressure in line 20) and the compressor discharge pressure (the pressure in line 40). It is also possible to use a venturi tube to reduce the pressure further, if desired.

Similarly, the temperature of the cold surface in the dew point sensor can be varied. The cold surface can be cooled using a Peltier cooling element (in which heat is removed from an electrical junction between two different metals), or by using the Joule-Thomson effect (where a fluid is cooled by throttling).

It may be desirable to cool the gas before it comes into contact with the cold surface. The sample of the compressed gas which is bled from the line 40 downstream of the compressor 30 will be hot, as a result of the compression which it has undergone, and it is possible that the gas will be so hot that it cannot be cooled sufficiently during the period in which it is in contact with the cold surface to allow condensation to take place.

Figure 3:
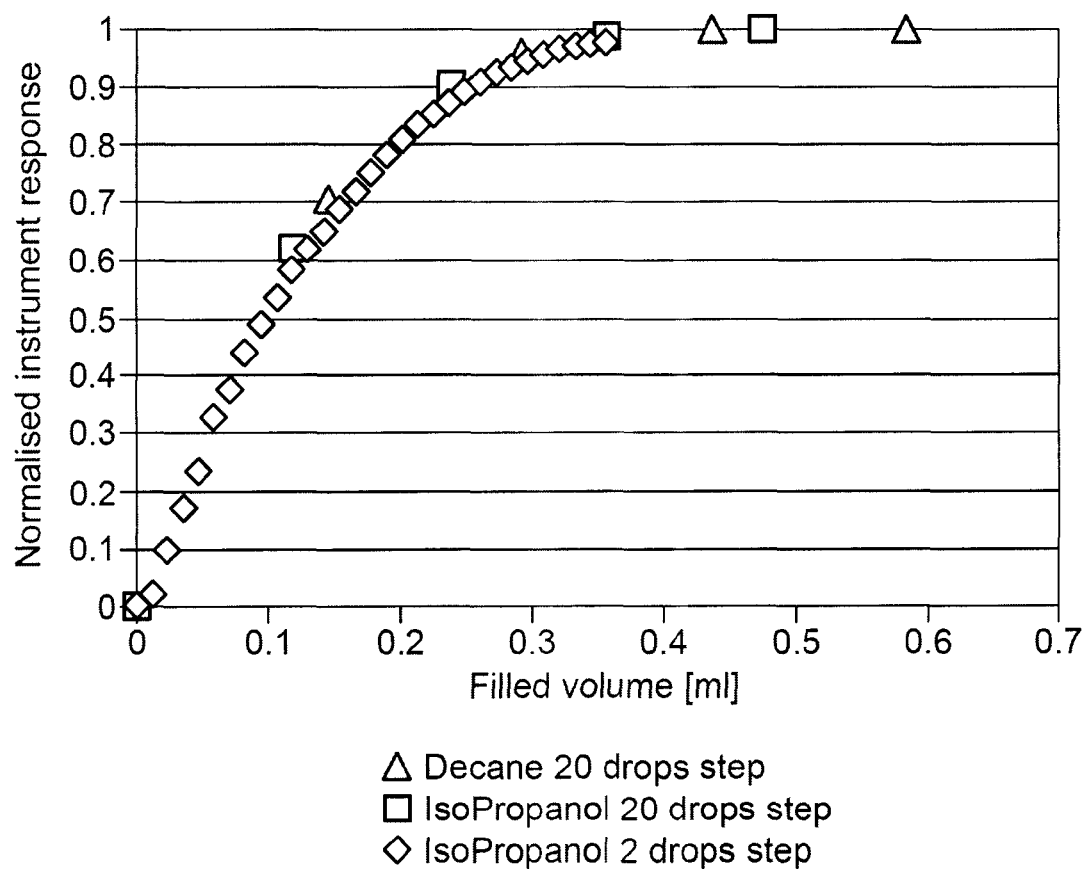
FIG. 3 is a graph relating to measurement of condensation rate using an oscillating u-tube densitometer.

A separate cooling apparatus may be provided to cool the gas, but this will increase the complexity and cost of the dew point monitoring apparatus. Thus, an option which may be preferred in some situations is to pass the sample back to the scrubber 10, and use the flow in the scrubber as a cold source in a heat exchanger, with the sample serving as the hot flow in the heat exchanger. Although this arrangement requires a little additional piping to be installed, it avoids the need to provide a separate cooling source and temperature regulation. FIG. 3 shows this arrangement in more detail.

By varying the pressure at the valve outlet and the temperature of the cold surface, the gas exiting the compressor 30 in line 40 can be subjected to a range of differing pressures and temperatures during its period in contact with the cold surface. The particular combination of pressure and temperature at which condensation occurs can be determined.

From this information and by using an appropriate equation of state, the amount of liquid in the gas exiting the compressor can be determined, and thus the degree of carryover from the scrubber can be determined.

In the presently preferred embodiment, the detection of condensation on the cold surface is carried out using optical means, and preferably near infra-red absorption or Raman spectroscopy. These methods have the advantage that the wavelengths used can pass through heavy oil, and are more robust with regard to deposition on or fouling of the cold surface in the dew point sensor.

Detection of condensation is initially an either/or process (that is, simply determining whether or not there is any condensation on the cold surface); the temperature and pressure at which condensation forms can then be used to determine the amount of liquid in the gas. Once the presence of condensation has been detected, it is possible to determine the nature of the liquid on the cold surface (for example, whether the liquid is water or a liquid hydrocarbon).

The embodiment described above is intended for dew point measurement, to determine the amount of liquid in a gas stream exiting a scrubber. However, the embodiment may be used to monitor the entire dew point line, including cricodenbar point (that is, the pressure in a two-phase system above which no gas can form, regardless of the temperature, and the fluid remains in a supercritical state).

The dew point sensor described above allows reliable measurements of the liquid fraction to be made, even when the liquid fraction is relatively small. With these measurements, it is possible to assure that the gas leaving the compressor is of the correct specification, and to monitor the performance of a separation unit (such as a scrubber) upstream of the compressor. If it is determined that the separation unit is allowing too much liquid to pass through, then steps can be taken to avoid damage to the compressor and to any equipment downstream thereof.

Figure 2:
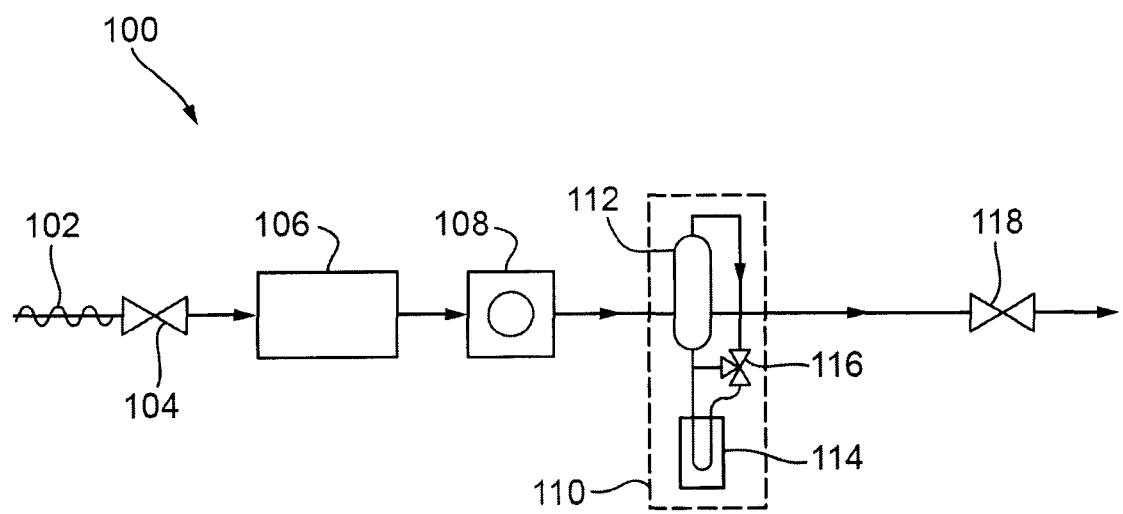
FIG. 2 is a schematic view of a liquid content monitoring apparatus.

FIG. 2 is a schematic view of a liquid content monitoring apparatus 100 which can be used in the invention, with its ancillary components.

As shown in FIG. 2, a sample is taken from a gas flow, the liquid content of which is to be measured. The sample is heated in a heater 102, to ensure that the fluid is in a supercritical state or is a superheated gas. The sample then passes through a pressure regulator 104 to change its pressure, and through a cooler 106 to change its temperature. The sample, with a specific pressure and temperature, then passes through an automatic dew point sensor 108. Flow, pressure and temperature are all automatically regulated, and so the measurement of the dew point can be automated.

After passing through the sensor 108, the sample is fed through a separator 110, where the liquid fraction is separated from the gas in chamber 112. The gas passes through a regulating valve 118, and is then returned to the gas flow at a lower pressure (such as at the suction side of a compressor). The amount of liquid can be measured, to provide further information on the amount of liquid in the flow, and can also be analyzed to determine the nature of the liquid. Measurement and analysis of the liquid can also be automatically regulated.

The liquid accumulates in a reservoir 114, and the reservoir can be flushed as necessary through operation of a valve 116. Liquid accumulation can be achieved by a set-up where the bottom of the chamber 112 has a funnel shape, so as to increase the change in height for a change in accumulated liquid volume. In a presently preferred form, the lower end of the funnel leads to the opening of a U-tube oscillator densitometer, which can be used to determine the nature of the accumulated liquid (water, hydrocarbon, etc). Further, the rate of filling of the densitometer can be used as a further measurement of the liquid content of the flow. FIG. 3 shows the relationship between partial filling and volume for two different fluids (decane and isopropanol) with different viscosities and differing rates of filling.

As the liquids being detected may not be stable under atmospheric conditions (they may flash when depressurized), the pressure in the liquid content monitoring apparatus (and the densitometer, if one is used) should be maintained such that the liquid detected remains in a liquid form.

Figure 4:
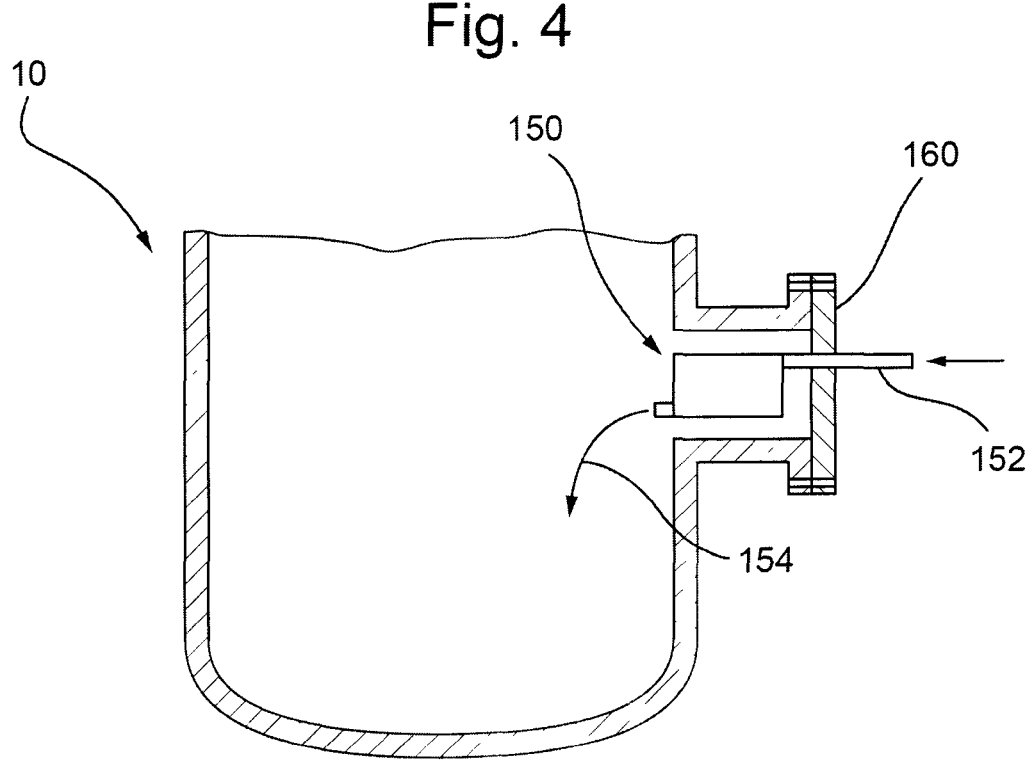
FIG. 4 is a schematic view of the liquid content monitoring apparatus arranged within the scrubber.

FIG. 4 shows an arrangement where the cooling in the liquid content monitoring apparatus is achieved using the flow of cool gas in the scrubber, as mentioned above.

The cooler, sensor and separator of FIG. 2 are schematically indicated by reference numeral 150 in FIG. 4. As can be seen, these parts are located within the scrubber 10, and can be accessed through a manhole lid 160. A line 152 for the sample passes through the manhole lid so that the sample can be passed to the liquid content monitoring apparatus. Further, if a densitometer is used to obtain information on the liquid in the sample, then this densitometer can be located either outside the scrubber or within the scrubber, and appropriate signal lines will also pass through the manhole lid. The gas and liquid from the sample can be discharged into the flow in the scrubber, as indicated by arrow 154.

FIGS. 5 to 9 show a combined cooler-separator 200 which can be used in the apparatus of FIG. 2. The cooler-separator cools the sample so that condensation takes place, and separates the condensed liquid from the gas. The condensed liquid can then be analyzed by a densitometer.

The cooler-separator 200 is in the form of a housing 210 with a cavity 220 therein, with a number of inlets and outlets communicating with the cavity. The housing is accommodated in a cold source such as a heat sink 230, which cools the cavity and thus the sample in the cavity. The sample enters at the top of the housing, and flows downwards through the cavity. As it flows downwards, the sample is cooled by the heat sink, to the point where condensation of liquid in the sample occurs. This condensation can be detected by any suitable means, and the condensed liquid can be collected, with the rate at which the condensed liquid accumulates serving as a measurement of the liquid content of the flow.

Figure 7:
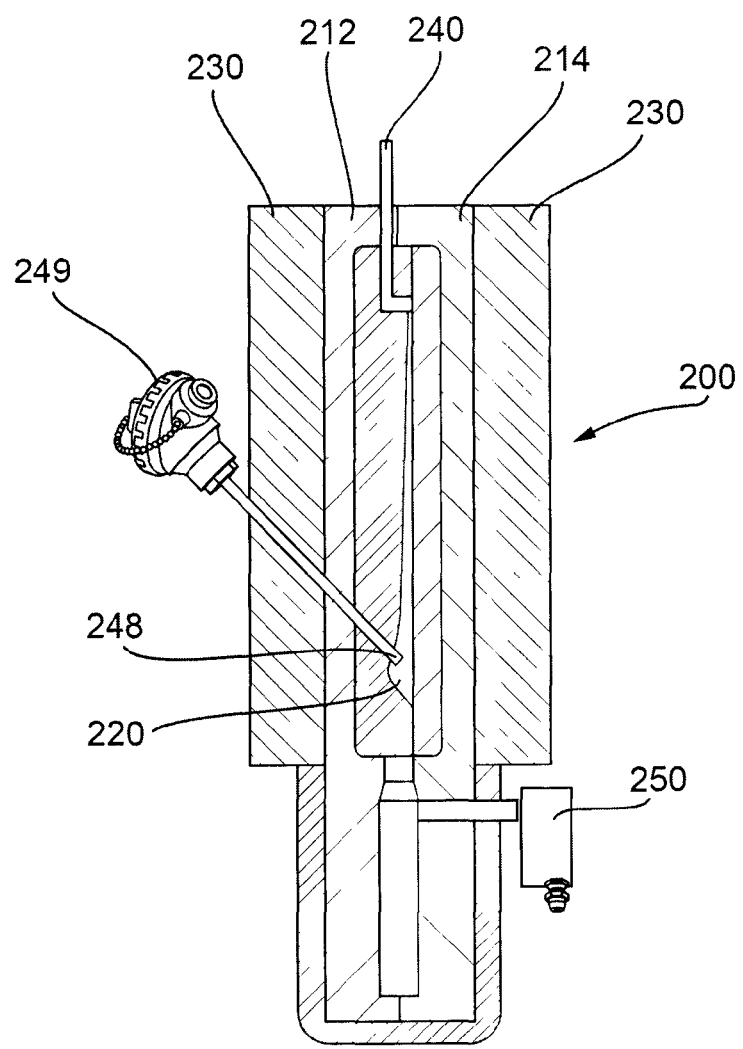
FIG. 7 is a cross-sectional view taken along line B-B in FIG. 6.
Figure 8:
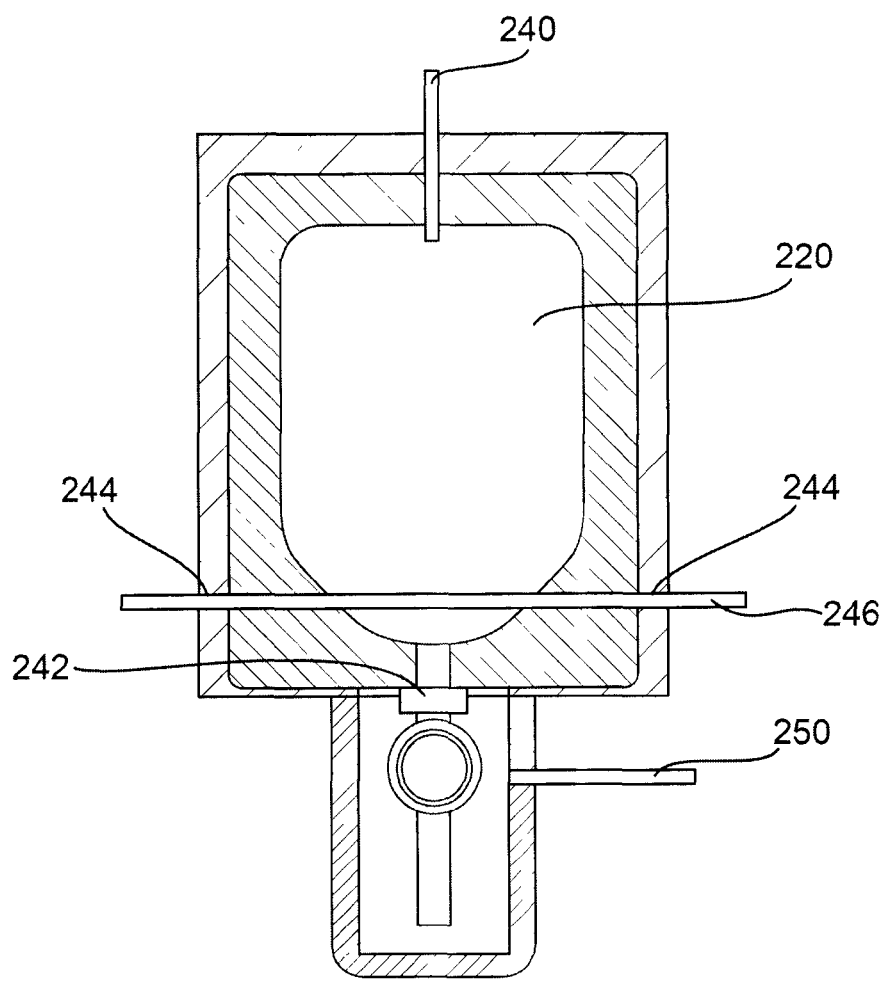
FIG. 8 is a cross-sectional view taken along line A-A in FIG. 5.

As best seen in FIGS. 7 and 8, the housing 210 is generally in the form of a rectangular parallelepiped, which in front view (shown in FIG. 8) is generally square-shaped, but slightly larger vertically than horizontally. FIG. 7 shows a side view, and it can be seen that the depth of the housing is considerably smaller than the vertical height and horizontal width.

As FIG. 7 shows, the housing 210 is formed from a front part 212 and a back part 214 (with the front part 212 being shown on the left in FIG. 7). A recess 222 is formed in the back surface of the front part 212, and when the front part 212 and the back part 214 are assembled, this recess confronts the flat facing surface 224 of the rear part to form the cavity 220. It is of course possible to form recesses in both the front part 212 and the back part 214.

The cavity 220 is shown in FIG. 8. In front view, the cavity 220 has a generally rectangular shape, but the lower part of the cavity tapers gradually towards the bottom, so that condensed liquid is guided towards an outlet 242 at the bottom of the cavity.

Figure 9:
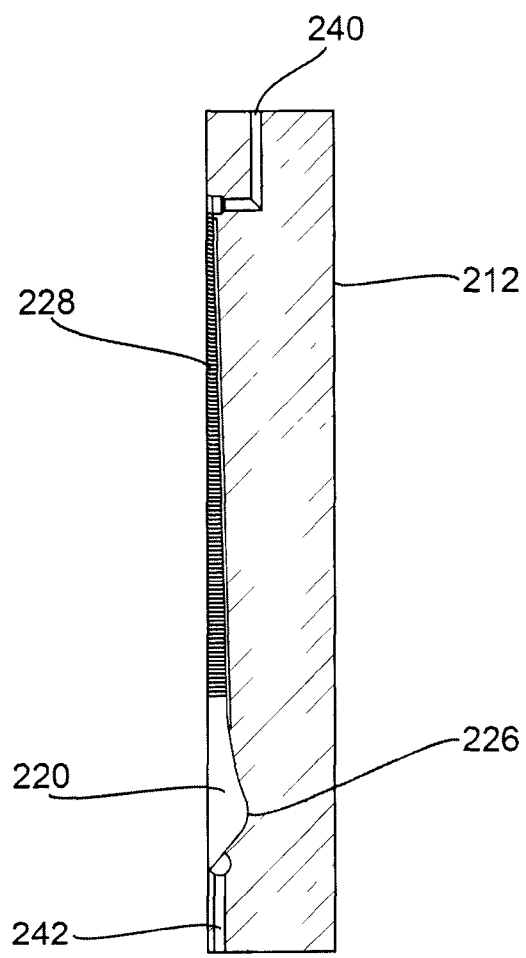
FIG. 9 is a cross-sectional view of a front part of the combined cooler-separator.

FIG. 9 is a cross-sectional view of the front part 212 of the housing, showing the recess 222 formed therein. It can be seen that the depth of the recess 222 increases gently as the distance from the top of the recess increases, until near the bottom of the recess. At this point, the depth of the recess increases more rapidly, so that the recess flares outwardly to a deepest point 226. The depth of the recess 222 then decreases to zero at the lowermost point of the recess. An outlet 242 for condensed liquid is provided at the bottom of the recess, and is connected to a suitable densitometer 250. A currently preferred densitometer is the L-Dens EX 437T from Anton Paar.

The recess 222 can be machined from the housing after the housing is formed; alternatively, the housing can be formed as a casting, with the recess being formed therein at the time of casting.

As also shown in FIG. 9, a very large number of posts 228, which extend in the front-to-back direction, are provided in the recess 222. These posts increase the internal surface area of the recess 222 which is in contact with the sample, and thus increase the heat transfer area. This increase in the heat transfer area is important as the cooling in the cooler-separator 200 is achieved by means of the heat sink 230 rather than by a more active cooling method. The posts can be of any suitable shape. If additional cooling is still required, then this can be achieved through the use of thermoelectrical elements using the Peltier effect.

If the recess is machined from the housing after the housing is formed, then the posts 228 can be formed in this machining stage. If the recess is integrally formed when the housing is cast, the posts can be formed by casting.

However, it is currently preferred for one or more inserts to be provided in the recess, with the posts being part of the inserts. The inserts are formed as a generally flat plate with a large number of posts projecting upwards. The inserts can then be accommodated in the recess to provide the necessary posts without the need for complex machining (of the housing or of the moulds used to cast it). Any suitable method can be used to for the inserts.

Figure 5:
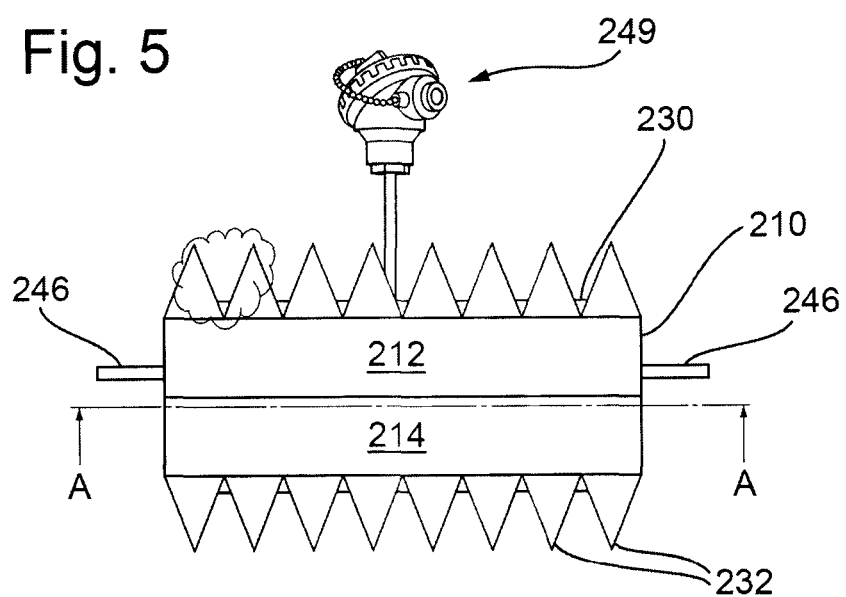
FIG. 5 is a plan view of a combined cooler-separator in combination with a heat sink.
Figure 6:
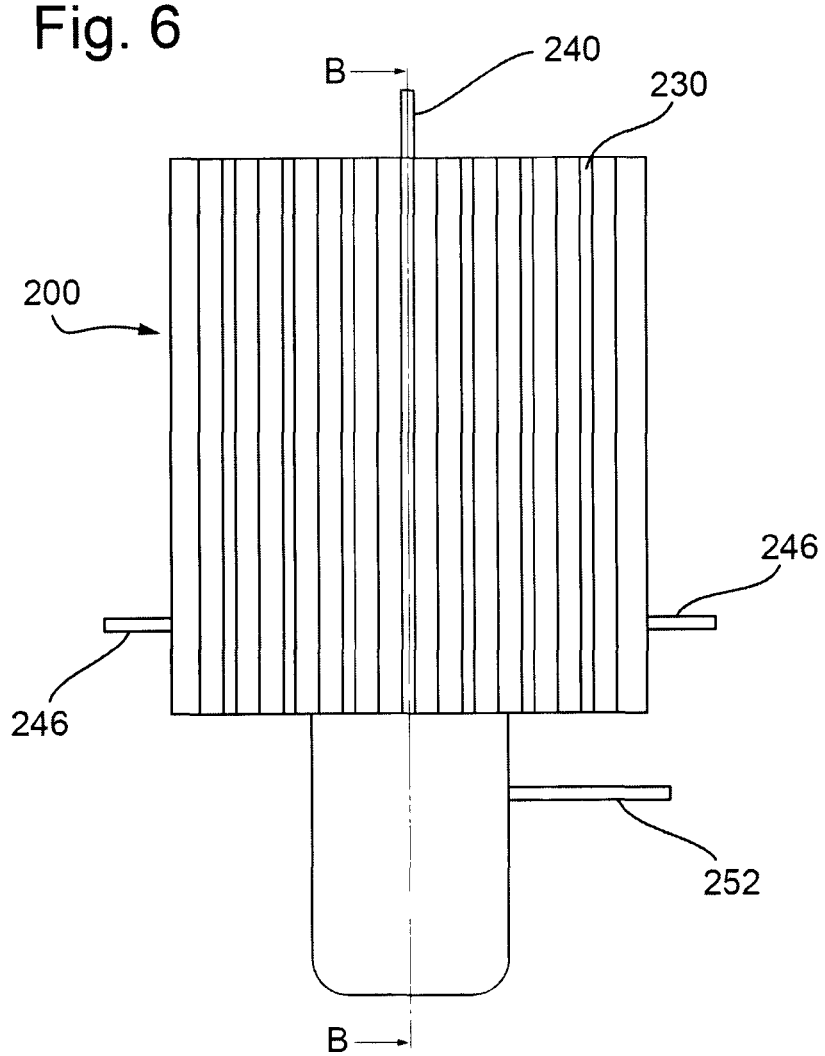
FIG. 6 is a side view of the combined cooler-separator in combination with the heat sink.

As best shown in FIGS. 5, 6 and 7, the housing 210 is located within a heat sink 230. The heat sink 230 is provided with fins 232 pointing away from the housing 210 to increase the area through which heat can be transferred away from the heat sink 230 (and thus the housing 210). As heat is transferred away from the heat sink, the cavity 220 is cooled.

As can be seen in FIGS. 6 and 8, an inlet 240 for the sample is provided at the top of the housing. The outlet 242 for the condensed liquid is located at the bottom of the housing, and communicates with the densitometer 250. An outlet for the liquid in the densitometer 250 is also provided, as indicated at 252.

Outlets for the cooled gas are provided at the sides of the housing, as indicated at 244. Preferably, a tube 246 extends between these two outlets, and a slot is provided in the bottom of the tube. Cooled gas can enter the tube 246 through the slot, and then flow away from the cooler-separator. In a preferred form, there is a gas flow in the tube 246, and this will tend to entrain the cooled gas into the tube.

An opening 248 for a temperature sensor 249 is also provided, as shown in FIG. 7. The opening 248 for the temperature sensor 249 is angled downwards, to avoid liquid accumulating therein, and is slightly above the gas outlet tube 246. The temperature sensor may also serve to sense the pressure in the cavity, so that the conditions at which condensation takes place can be determined.

As the temperature gradients within the cooler-separator are preferably kept to a minimum, it is preferably installed downstream of a pre-cooler. The pre-cooler carries out most of the cooling of the sample necessary for dew-point measurement (around 90 to 95%), but the outlet temperature of the pre-cooler should be above the dew-point temperature. The specific form of the pre-cooler is not important to the invention, and so the pre-cooler will not be described further.

As an alternative to using a heat sink, the cooler-separator could be mounted near an alternative cold source, such as a flow of relatively cool gas in a scrubber as shown in FIG. 1 and FIG. 4. The cool gas in the scrubber will cool the cavity, which leads to the liquid in the gas condensing, and the condensed liquid can then be analyzed in the densitometer. The gas and the condensed liquid can then be discharged into the flow in the scrubber.

As with the liquid content monitoring apparatus of FIG. 2, the cooler-separator and the densitometer should be maintained at a pressure such that such that the liquid detected remains in a liquid form.

The apparatus as described with reference to FIG. 2 is effectively an automated apparatus for carrying out the method described in ISO 6570 ("Natural gas—Determination of potential hydrocarbon liquid content—Gravimetric methods"). Automation of the process allows for online monitoring of the liquid content, and is well suited for assessing carryover from scrubbers. Further, since the process is automated and can be carried out without any human intervention, it can be used to monitor liquid content in flows which are normally inaccessible to humans.

In addition, the gas from the sample is returned to the original flow, rather than being flared or dumped to atmosphere. The process can therefore be used to monitor liquid content in situations such as a subsea environment, where flaring is not possible.

The invention claimed is:

1. A method of determining an amount of liquid in a gas stream exiting a scrubber in a natural gas processing facility, wherein the natural gas processing facility comprises a superheating unit directly downstream of the scrubber, the method comprising the steps of:

separating the gas stream from a two-phase fluid using the scrubber;

passing the gas stream from the scrubber to the superheating unit;

taking a sample of fluid from the superheated gas stream downstream of the superheating unit, the fluid being in a supercritical state or a superheated gas;

passing the sample through a regulating arrangement to vary the flow rate and pressure of the sample, and passing the sample through a device to vary the temperature of the sample; and measuring a rate of liquid condensation formed from the sample fluid as the temperature and pressure are varied, wherein the variation of the pressure and temperature and the measurement of the rate of liquid condensation are carried out automatically.

2. The method as claimed in claim 1, wherein the superheating unit is a compressor.

3. The method as claimed in claim 1, wherein the superheating unit is a heater.

4. The method as claimed in claim 1, wherein the temperature of the sample is reduced by passing the sample back to the scrubber, which serves as the device for varying the temperature, and wherein the scrubber is used as a cold source in a heat exchanger with the sample as the hot fluid.

5. The method as claimed in claim 1, wherein the measurement of the rate of liquid condensation is carried out by a densitometer.

6. A system for carrying out the method of claim 1.

* * * * *